US009849253B2

United States Patent
Young

(10) Patent No.: US 9,849,253 B2
(45) Date of Patent: Dec. 26, 2017

(54) TEMPERATURE CHANGING INTRACORPOREAL FLUID DELIVERY SYSTEM

(71) Applicant: Forever Young International, Inc., Henderson, NV (US)

(72) Inventor: Daniel L. Young, Henderson, NV (US)

(73) Assignee: Forever Young International, Inc., Las Vegas, NV (US)

( * ) Notice: Subject to any disclaimer, the term of this patent is extended or adjusted under 35 U.S.C. 154(b) by 674 days.

(21) Appl. No.: 14/358,977

(22) PCT Filed: Oct. 29, 2013

(86) PCT No.: PCT/US2013/067351
§ 371 (c)(1),
(2) Date: May 16, 2014

(87) PCT Pub. No.: WO2014/070798
PCT Pub. Date: May 8, 2014

(65) Prior Publication Data
US 2014/0323969 A1 Oct. 30, 2014

Related U.S. Application Data

(60) Provisional application No. 61/719,946, filed on Oct. 29, 2012.

(51) Int. Cl.
*A61M 5/44* (2006.01)
*A61M 5/14* (2006.01)

(52) U.S. Cl.
CPC .................. *A61M 5/44* (2013.01); *A61M 5/14* (2013.01); *A61M 2005/1416* (2013.01);
(Continued)

(58) Field of Classification Search
CPC ........ A61M 5/14; A61M 5/1401; A61M 5/44; A61M 5/445; A61M 2005/1416;
(Continued)

(56) References Cited

U.S. PATENT DOCUMENTS 4,874,033 A * 10/1989 Nicholas Marchiani Chatelain .............. A61M 5/445 165/11.1
5,220,909 A * 6/1993 Pickard .............. B65D 81/3484 126/246

(Continued)

FOREIGN PATENT DOCUMENTS

EP 0309964 A2 4/1989
FI 896 072 A 6/1991

(Continued)

OTHER PUBLICATIONS

International Search Report and Written Opinion dated Jan. 29, 2014 in related International Patent Application No. PCT/US2013/067351.

(Continued)

*Primary Examiner* — Kami A Bosworth
(74) *Attorney, Agent, or Firm* — Troutman Sanders LLP

(57) ABSTRACT

An intracorporeal temperature changing intracorporeal fluid delivery device is described that includes an outer shell forming an internal enclosure comprises at least one heat generation layer and a heater activation system. In one embodiment, the invention is a intracorporeal fluid delivery device, such as an intravenous fluid device. As such it is generally configured for delivery of a heated fluid to a user, and is configured to be worn about an appendage of the user such as an arm, leg, or neck or otherwise operatively connected to a user.

18 Claims, 6 Drawing Sheets

(52) U.S. Cl.
CPC ............... *A61M 2205/0277* (2013.01); *A61M 2205/364* (2013.01); *A61M 2209/088* (2013.01)

(58) Field of Classification Search
CPC ........ A61M 2005/36; A61M 2005/364; A61M 2205/127; A61M 2209/088
USPC .................................................. 604/6.13, 113
See application file for complete search history.

(56) References Cited

U.S. PATENT DOCUMENTS

| | | | | |
|---|---|---|---|---|
| 5,250,032 | A * | 10/1993 | Carter, Jr. ................ | A61M 5/44 219/535 |
| 5,263,929 | A | 11/1993 | Falcone | |
| 2003/0060762 | A1* | 3/2003 | Zvuloni ................. | A61B 18/02 604/113 |
| 2004/0254532 | A1* | 12/2004 | Mehier ................... | A61B 18/04 604/113 |
| 2008/0039815 | A1* | 2/2008 | Ogawa ..................... | A61M 5/44 604/408 |
| 2008/0077087 | A1 | 3/2008 | Martens | |
| 2009/0043366 | A1 | 2/2009 | Dae | |
| 2010/0219090 | A1* | 9/2010 | Thatcher ................ | A45C 11/38 206/316.1 |
| 2011/0224760 | A1* | 9/2011 | Potter ................... | A61F 7/0097 607/104 |
| 2012/0210996 | A1 | 8/2012 | Goding | |
| 2013/0026248 | A1* | 1/2013 | Paulsen ..................... | A45F 5/00 239/1 |
| 2013/0226087 | A1* | 8/2013 | King ....................... | A61M 5/44 604/113 |
| 2013/0233283 | A1* | 9/2013 | Rinke ................ | F02M 37/0035 123/495 |
| 2013/0267930 | A1 | 10/2013 | Robson et al. | |

FOREIGN PATENT DOCUMENTS

| | | |
|---|---|---|
| GB | 2485380 A | 5/2012 |
| JP | 56061549 A | 5/1981 |
| JP | 62021323 U | 2/1987 |
| JP | 62268558 A | 11/1987 |
| JP | 64025853 A | 1/1989 |
| JP | 2001000230 A | 1/2001 |
| JP | 2001299248 | 10/2001 |
| JP | 2004202166 A | 7/2004 |
| JP | 2005514989 A | 5/2005 |
| WO | 2012037037 A1 | 3/2012 |
| WO | 2012054973 A1 | 5/2012 |

OTHER PUBLICATIONS

International Preliminary Report on Patentability dated May 5, 2015 in related International Patent Application No. PCT/US2013/067351.

* cited by examiner

TEMPERATURE CHANGING INTRACORPOREAL FLUID DELIVERY SYSTEM

FIELD

The following description relates generally to fluid delivery devices, such as intracorporeal fluid delivery devices. In one embodiment, the device is configured for delivery of a heated intracorporeal fluid to a user, and is configured to be worn as a "sleeve" about an appendage of the user or otherwise in operative contact with the user.

BACKGROUND

Intracorporeal delivery of fluids to a patient is a common method for administering treatments for countless medical conditions. The fluids may be delivered intravenously, intraperitoneally, or the like. In addition to their use in hospitals, such heated fluid therapy is commonly administered in the field by first responders such as paramedics and certified members of search and rescue teams. Although intravenous therapy is an ideal method of rapidly delivering fluid medication, hydration or sustenance to a patient, in an outdoors emergency situation where access to medical equipment or external power means is limited, the patient may be dangerously cold and at risk of developing circulatory shock. In this situation, it may be counterproductive and potentially harmful to administer intracorporeal therapy if the source of fluid for delivery is significantly colder than the patient's normal body temperature.

For example, in the case of first responders who first reach a victim of accident or a victim of exposure in a remote environment, any fluids for intravenous therapy carried by the responders to the victim may become cold during the journey to the victim. In these situations where the first responders must travel to reach the victim, immediate intravenous delivery of fluids such as electrolytes, plasma or medication may be critical to the survival of the victim. However, intravenous delivery of cold fluids (i.e. fluids that have become cold or are otherwise unheated) may lower the victim's body temperature and precipitate circulatory shock. In addition, the devices of the present device may aid in raising the core temperature of a person already in shock.

Accordingly, there is a need for a device and a system capable of rapidly heating intracorporeal fluids for delivery to a patient to eliminate the risk of body temperature lowering by administration of therapy due to delivered cold fluids. Ideally, the device and the system should be lightweight, portable, relatively fast to activate and heat, easy to use and not require an external power source. The embodiments disclosed below satisfy these needs.

SUMMARY

The following simplified summary is provided in order to provide a basic understanding of some aspects of the claimed subject matter. This summary is not an extensive overview, and is not intended to identify critical or essential elements, or to delineate the scope of the claimed subject matter. Its purpose is to present the disclosed embodiments in a simplified form as a prelude to the more detailed description that follows.

In one embodiment, the device of the present invention is an intracorporeal fluid delivery device for heating the temperature of a fluid to be administered to a patient, the device that comprises: an outer shell, wherein the outer shell comprises an inner impermeable layer with an activation aperture, and an outer layer, wherein the inner layer and the outer layer form an internal enclosure within the outer shell. A first heat generation layer is disposed inside the internal enclosure, wherein the first heat generation layer comprises at least one liquid permeable heater comprising a first exothermic reactant. An intracorporeal fluid conduit is disposed within or adjacent to the outer shell, wherein the intracorporeal fluid conduit has a path through the device, and wherein the intracorporeal conduit further comprises an inlet port adjacent to a proximal end of the device and an outlet port adjacent to a distal end of the device. A heater activation system comprises at least one sealed bladder disposed inside the internal enclosure adjacent to the first heat generation layer. An activator liquid is disposed in the at least one sealed bladder, wherein the activator liquid when released from the at least one sealed bladder contacts the first heat generation layer and permeates the at least one liquid permeable heater to combine with the first exothermic reactant causing an exothermic reaction that heats the intracorporeal fluid in the conduit.

In some embodiments, the device further comprises a fastener configured to attach the device around an appendage of a user device of the present invention may also include fasteners which allow it to be attached around the appendage of a user. In other embodiments, the device further comprises an activation strip operatively connected to the at least one sealed bladder, wherein the activation strip comprises a handle segment extending from the outer shell through the activation aperture into the at least one sealed bladder. Accordingly, pulling the handle segment unseals the at least one sealed bladder and releases the activator liquid.

In some embodiments, the distal end of the device comprises a thumb-receiving aperture for holding the device in place when disposed on an appendage of a user. In other embodiments, further comprising an outlet tube mechanically connected to the outlet port of the intracorporeal fluid conduit in fluid communication with a vein of a user, wherein the intracorporeal fluid is an intravenous fluid. In other embodiments, the device further comprises an inlet tube mechanically connected to the inlet port of the intracorporeal fluid conduit in fluid communication with a vein of a user, wherein the intracorporeal fluid is an intravenous fluid.

Still in other embodiments, the outer layer of the outer shell comprises a fabric layer external to the impermeable layer, wherein the intracorporeal fluid conduit is disposed between the impermeable inner layer and the outer fabric layer. The intracorporeal fluid conduit may be attached to the outer shell inside the internal enclosure and/or routed non-linearly between the inlet port and the outlet port.

In other embodiments, the device further comprises a temperature control system. The temperature control system comprises a cooling inlet conduit in fluid communication with a source of fluid with an associated fluid temperature, wherein the associated fluid temperature is below a body temperature of a user. A heating inlet conduit is in fluid communication with the outlet port of the intracorporeal fluid conduit. The cooling inlet and the heating inlet are in fluid communication with a mixer valve. The mixer valve is configured to regulate fluid flow into and out of the temperature control system. An outlet conduit is in fluid communication with the mixer valve such that the a mixer valve is configured to selectively provide for the outlet conduit to be in fluid communication with only the cooling inlet conduit, only the heating inlet conduit, or both the heating and cooling inlet conduits. In some embodiments, the mixer valve is configured to manually selectively provide for the outlet conduit to be in fluid communication with only the cooling inlet conduit, only the heating inlet conduit, or both the heating and cooling inlet conduits. In other embodiments, further comprises a bimetallic strip disposed inside the mixer valve that is configured to automatically selectively regulate a volume of fluid flowing through and provide for the outlet conduit to be in fluid communication with only the cooling inlet conduit, only the heating inlet conduit, or both the heating and cooling inlet conduits.

In other embodiments, the device further comprises at least two heat generation layers, each exhibiting a different heating profile. Still in other embodiments, the heat generation layer further comprises at least one second liquid permeable heater comprising a second exothermic reactant, wherein the activator liquid contacts the heat generation layer and permeates the at least one second liquid permeable heater to combine with the second exothermic reactant causing a second exothermic reaction that heats fluids in the intracorporeal fluid conduit to a second predetermined temperature for a second predetermined length of time. Accordingly, the first predetermined temperature is greater than the second predetermined temperature and the first predetermined length of time is less than the second predetermined length of time which allows for the device instantly self-heat and sustain the heating for relatively long duration of time.

In other embodiments, a temperature changing intracorporeal fluid delivery system comprises a source of fluids such as an intravenous fluid bag as well as the device described herein. Accordingly, the source of fluids is in fluid communication with the device and configured to deliver heated fluids to a user.

The following describes another embodiment where the device is configured as an intraveneous fluid delivery sleeve:

A self-heating intravenous fluid delivery sleeve includes a pliable outer shell with opposing portions and an impermeable layer forming an internal enclosure with an activation aperture. The outer shell includes a fastener that is configured to attach the opposing portions of the outer shell to each other to form a sleeve. The sleeve in certain embodiments can be tubular and have an outward facing outer wall and inward facing inner wall. The sleeve may also have a proximal end and a distal end. A first heat generation layer is disposed inside the internal enclosure of the outer shell and includes at least one liquid permeable heater containing an exothermic reactant. An intravenous fluid conduit is attached to the outer shell internal to the first heat generation layer and has an inlet port that is adjacent to the proximal end of the sleeve and an outlet port that is adjacent to the distal end of the sleeve.

The intravenous fluid delivery sleeve also includes a heater activation system with a sealed first bladder that is disposed inside the internal enclosure of the outer shell and adjacent to the first heat generation layer. The heater activation system also includes an activator liquid that is disposed internal to the first bladder. An activation strip with a handle segment is operatively connected to the first bladder, wherein the handle segment extends external to the outer shell through the activation aperture. Pulling on the handle segment of the activation strip unseals the bladder and releases the activator liquid into the internal enclosure formed by the outer shell where the activator liquid contacts the heat generation layer and permeates the at least one liquid permeable heater to combine with the exothermic reactant causing an exothermic reaction that heats the intravenous fluid conduit.

The distal end of the sleeve may have a thumb-receiving aperture for holding the sleeve in place when disposed on an appendage of the user, and for bracing the sleeve against movement so as to prevent strain of any attached intravenous conduits. The sleeve may be disposed on the following appendages of a user: arm(s), leg(s), neck or the like. The sleeve may further comprise an outlet tube whereby the outlet tube would be connected to the outlet port. The outlet tube in this embodiment would be in fluid communication with a vein of the user. An inlet tube may also be connected to the inlet port of the intravenous fluid conduit. The inlet tube would be in fluid communication with a source of fluid for intravenous delivery to the user.

The outer shell of the sleeve may further include an outer fabric layer external to the impermeable layer that forms the internal enclosure. In this embodiment, the intravenous fluid conduit may be attached to the outer shell between the impermeable layer and the outer fabric layer inward from the heat generation layer. The intravenous fluid conduit may also be attached to the outer shell inside the enclosure formed by the impermeable and inward from the heat generation layer. The intravenous fluid conduit may be routed in a tortuous, non-linear pathway (i.e. tortuously) along the outer shell between the inlet port and the outlet port.

In another embodiment, an instant self-heating intravenous fluid delivery sleeve has a pliable outer shell with opposing portions and an impermeable layer forming an internal enclosure with an activation aperture. Also provided is a fastener that is configured to attach the opposing portions of the outer shell to each other to form a sleeve. The sleeve may be tubular but may also take other shapes as may be required by the appendage or feature to which it attaches. Further, the sleeve may have an outward facing outer wall and inward facing inner wall. A conduit holder on the inner wall of the sleeve is used to hold an intravenous fluid conduit along the inner wall. A heat generation layer inside the internal enclosure of the outer shell includes a liquid permeable heater containing an exothermic reactant.

In some embodiments, the sleeve may further include a heater activation system. The heater activation system can include a sealed bladder that is disposed inside the internal enclosure and adjacent to the heat generation layer. The heater activation system may contain an activator liquid. An activation strip is operatively connected to the bladder and has a handle segment extending outside the outer shell. Pulling on the handle segment of the activation strip unseals the bladder and releases the activator liquid into the enclosure where it contacts the first heat generation layer and permeates a liquid permeable heater to combine with the exothermic reactant. This causes an exothermic reaction that instantly heats the intravenous fluid conduit that is mounted to the inner wall of the sleeve.

In order to thoroughly explain various structural and functional features and advantages of the foregoing embodiments, various illustrative examples are described below in connection with the attached drawings. However, these features and advantages are only intended to be exemplary and do not represent every possible structure and function that may be incorporated in various embodiments falling within the scope of the claims that follow this description. Accordingly, other advantages and novel features of the claimed embodiments may become apparent from the following description considered with reference to the attached drawings.

DETAILED DESCRIPTION

A self-heating intracorporeal fluid delivery device includes an outer shell and an impermeable layer which can be used in a flat configuration or rolled up to form an internal enclosure. In one embodiment, the device includes an activation aperture. The outer shell contains at least one heat generation layer and a heater activation system. The outer shell may include a fastener for joining opposing portions of the outer shell to each other to form a sleeve or other similar shape to enclose an appendage. The sleeve in certain embodiments can be tubular or take other shapes as may be required by the appendage or object to which the sleeve attaches. An intracorporeal conduit is associated with the device and is attached to the outer or inner shell or is contained therebetween. The conduit further includes an inlet port and an outlet port. In one embodiment, activation may be effectuated via an activation strip with a handle segment that is operatively connected to at least one sealed bladder. From the at least one sealed bladder, the activation strip extends outside and external to the outer shell through the activation aperture. Accordingly, pulling on the activation strip causes the heater activation system to activate the heat generation layer, generating and transferring heat to the fluid flowing through the conduit. Throughout this disclosure, the term "user" may refer to either a patient receiving intracorporeal therapy and/or someone or something administering such therapy to another patient.

Figure 1:
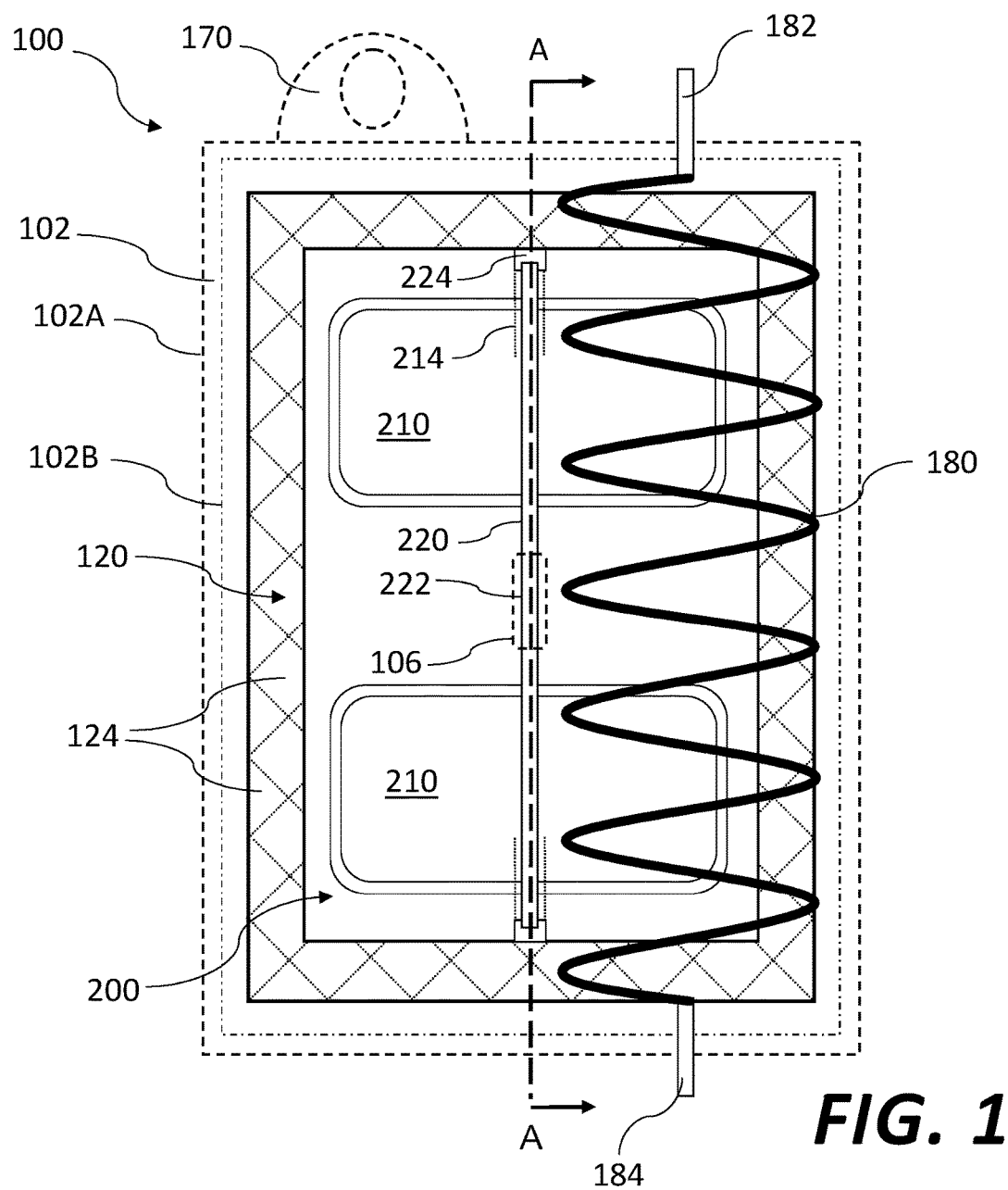
FIG. 1 is a top plan view of a self-heating intravenous fluid delivery device shown in a flat configuration with outer shell layers shown only in hidden lines for clarity.

FIG. 1 shows a self-heating fluid delivery device 100 laid flat and not installed on an appendage of a user. In such an embodiment, the device 100 may be laid directly on the user, such as on the chest or abdomen. In this configuration, device 100 is formed as a generally flat sheet or panel with outer shell 102. However, it is not essential for the sheet to remain flat as it can adapt to the surface on which it rests. Outer shall 102 may comprise an outer fabric layer 102A and an inner impermeable layer 102B. In order to maintain clarity in the drawings, outer shell 102 is only depicted in dashed lines so that internal structures are visible. Outer shell 102 forms internal enclosure 105 (depicted in FIG. 2A) with an inner wall comprising impermeable layer 102B. Outer shell 102 includes activation aperture 106 which, in some embodiments, provides fluid communication from internal enclosure 105 to outside of outer shell 102. Outer shell 102 may also include thumb aperture 170 and optional fasteners 190 (shown in FIG. 3.) However, thumb aperture 170 may be absent or configured so that other methods of grasping or grabbing the sleeve 100 are possible, including using fingers other than a thumb or providing a handle or other equivalent that provides a user with the capability of grabbing the sleeve 100. The fastener 190 may include a hook-and-loop fastener, adhesive strips, finger/thumb loops, or any other suitable fastening structure.

Figure 2A:
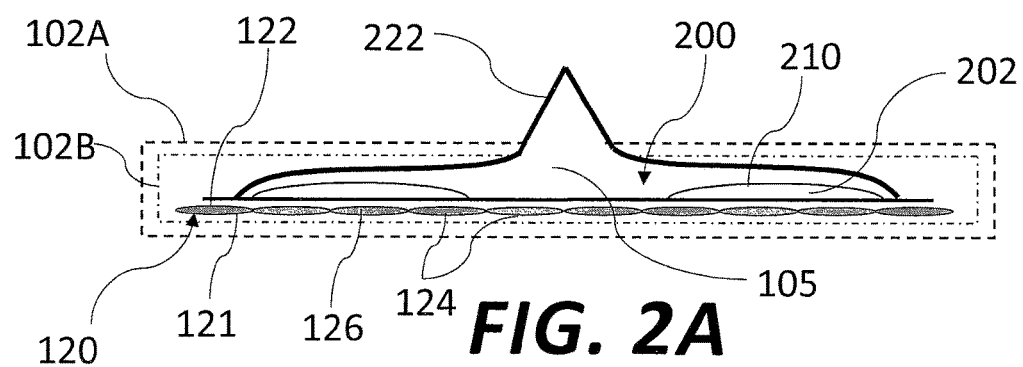
FIGS. 2a and 2b is a cross-sectional view of the embodiment of FIG. 1 taken along line A-A.

Referring now to FIGS. 1 and 2A, disposed inside internal enclosure 105 is at least one heat generation layer 120 and heater activation system 200. Heat generation layer 120 includes substrate layer 121 and one or more covering layers 122, both of which may be formed from a liquid permeable material. Covering layer 122 is attached to substrate layer 121 to form at least one liquid permeable heater 124. For example, as shown in FIGS. 1 and 2, heat generation layer 120 may be a quilted structure with covering layer 122 quilted to substrate layer 121 to form a plurality of chambers impregnated with first exothermic reactant 126. Each such chamber is one liquid permeable heater 124. In other embodiments, heaters 124 may be formed as large pouches of covering layer 122 attached to substrate layer 121 and may contain first exothermic reactant 126.

The substrate layer 121 of the heat generation layer 120 may include a reactive mineral compound of super absorbent polymer with magnesium and iron such that with the introduction of an activator liquid 202 such as water and/or necessary salts, an exothermic reaction occurs and produces heat. The salt may be included in the reactive mineral compound, or it may be added to the water used to activate the reactive mineral. The incorporation of a super absorbent polymer within the compound provides a number of unusual and unexpected key advantages. For instance, the presence of the super absorbent polymer buffers the reaction so that the reaction is less violent than the reaction would be without the polymer additive. Also, because the super absorbent polymer attracts water molecules which can then be drawn out for reaction with the active mineral compound, the chemical reaction lasts far longer than a compound without the polymer.

Heater activation system 200 includes one or more sealed bladders 210. Each bladder 210 may contain activator liquid 202 and each bladder 210 may be disposed adjacent to heat generation layer 120. Bladders 210 may be formed as chambers or pouches within a laminated sheet, panel, or equivalent comprising impermeable layers. Accordingly, bladders 210 may be constructed from materials such as polymeric sheets and/or metallic foils. Each bladder 210 may include a pre-weakened (via laser or the like) failure region 214 which is designed to easily shear, rupture, unseal or otherwise open when acted upon by starter element 220. In this embodiment, starter element 220 is an elongate activation strip with unsealing segment 224 that is operatively connected to region 214 and handle segment 222 extending through activation aperture 106 outside outer shell 102. To activate the heater activation system 200 of the device 100, a user grasps handle segment 222 of starter element 220 and pulls. This force applied by pulling is transmitted to failure region 214 of each bladder 210 causing each bladder 210 to open/unseal and release activator liquid 202 onto heat generation layer 120. The activator liquid 202 then permeates one or more heaters 124 and combines with exothermic reactant 126 thereby causing an exothermic chemical reaction that generates heat. In addition to the starter element being an elongate activation strip, the device 100 may employ twisting elements, plungers, piercers or the like to cause the bladder 210 open, unseal, or otherwise rupture in order to release activator liquid 202 which thereafter permeates one or more heaters 124.

Device 100 also includes a conduit 180 to which heat can be transferred from heat generation layer 120. In the illustrated embodiment of FIG. 1, the conduit takes a non-linear and extended path from the top edge to the bottom edge of the device 100 (i.e., the conduit 180 travels at least twice the distance from top to bottom since the path is curved). In some embodiments, intravenous conduit 180 is attached to the outside of outer shell 102 with a fastener, adhesive or other suitable mounting mechanism or holder, but in the illustrated embodiment conduit 180 is disposed inside outer shell 102. For example, conduit 180 may be disposed between outer layer 102A and inner impermeable layer 102B. Alternatively, conduit 180 may be disposed internal to impermeable layer 102B that is inside internal enclosure 105 and contacts heat generation layer 120 and/or heater activation system 200. Conduit 180 may be routed along a tortuous pathway (as shown in FIG. 1) in order to increase the total surface area available for heat transfer to a fluid flowing inside conduit 180. However, in other embodiments, conduit 180 may be routed along a series of heating rows oriented horizontally or vertically or in a zigzag pathway. For the sake of clarity, conduit 180 is simply shown in solid black lines even though in various embodiments it may be inside (and therefore obscured by) outer shell 102, or beneath (and therefore obscured by) one or more of heat generation layers 120 or heat activation system 200.

As shown in FIG. 1, the device 100 may further include inlet port 184 located at the proximal end of the device 100 and outlet port 182 located at the distal end of the device 100. Inlet port 184 may be connected to and in fluid communication with a source of intracorporeal fluid such as volume expanders including crystalloids and colloids, blood-based products for blood transfusions, blood substitutes, buffer solutions to correct certain deficiencies, certain medications that can be delivered intravenously, and nutritional formulas for use in parenteral delivery. Accordingly, any of the above may be contained in a source of fluids such as a fluid bag or other storage means thereby functioning as the source of intracorporeal fluid to be delivered to a patient. Outlet port 182 may be connected to and in fluid communication with a conduit with a hypodermic needle or shunt or the like in fluid communication with a blood vessel or tissue of a user or a patient.

Figure 3:
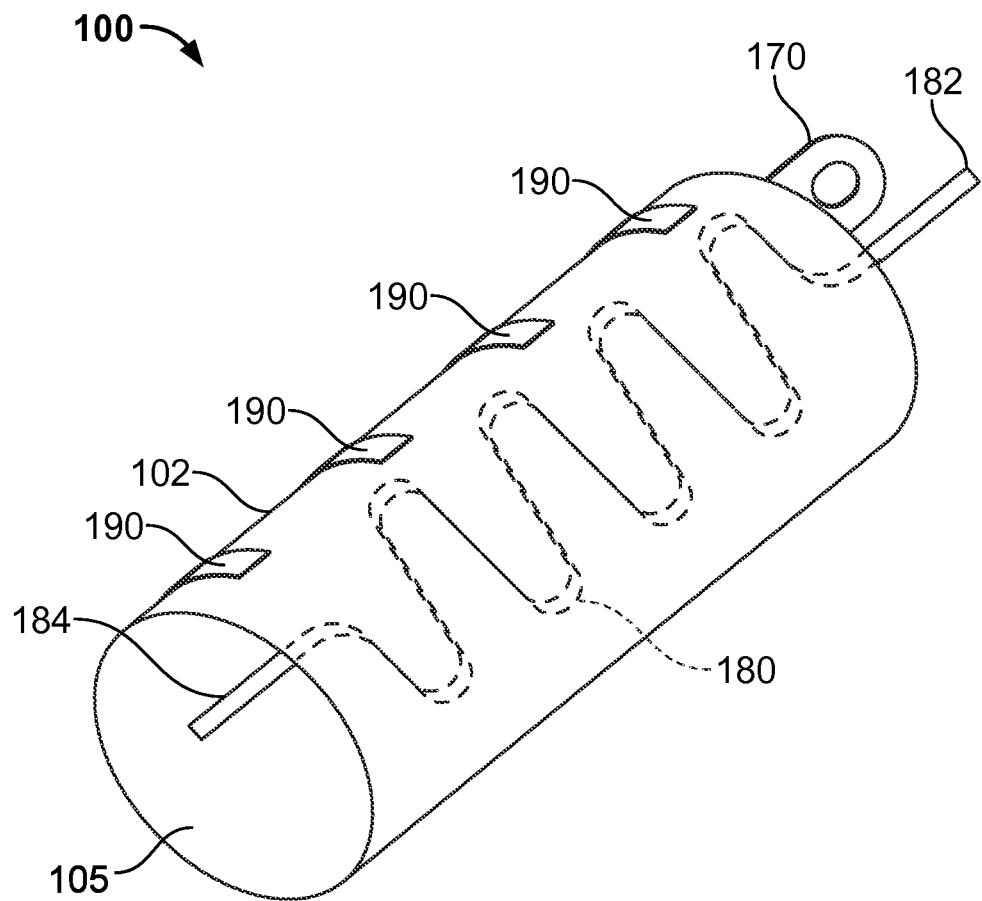
FIG. 3 shows the embodiment of FIG. 1 in a sleeve configuration.

To use device 100 in the form of a "sleeve", an appendage of a user may be placed along outer shell 102 and generally aligned with the direction of flow of conduit 180. In other words, the user's arm, leg, neck or other appendage is oriented with the hand (or foot) adjacent to outlet port 182 and the upper arm (or upper leg) is adjacent to inlet port 184. In this embodiment, sleeve 100 is installed on the appendage of a patient by wrapping outer shell 102 around the appendage and fastening it into a tubular structure with fasteners 190 as shown in FIG. 3. The tubular structure of device 100 in the form of a sleeve thus has inner walls that contact the skin of a user and outer walls that face away from the user. In some embodiments, conduit 180 is routed closer to the inner walls while in other embodiments it is routed closer to the outer walls. Further, heat generation layer 120 and heater activation system 200 may be disposed in any possible position relative to conduit 180. For example, they may be disposed between the user's appendage and conduit 180, or conduit 180 may be disposed between heat generation layer 120 (and/or heater activation system 200) and the user's appendage.

A source of fluid (as described above) for intravenous delivery is connected to inlet port 184 and a conduit connected to a blood vessel is connected to outlet port 182. In this embodiment, the device 100 is activated by pulling on handle segment 222 (as explained above), which initiates an exothermic reaction that transfers heat to the fluid flowing transfer of heated fluid to the user/patient via conduit 180.

Following activation of the exothermic reaction, the heated temperature of the device 100 and fluid flowing out of conduit 180 may be predetermined by providing multiple different and/or removable heat generation layers 120 with different mixtures of exothermic reactant 126. Adjusting the number of heat generation layers 120 and/or differing mixtures of exothermic reactant serves as a mechanism by which the user may regulate the amount of heat that is generated. The appropriate heat generation layer 120 for any situation may be selected by a user and inserted into enclosure 105 prior to use of the sleeve 100.

In FIG. 2A as described above, heat generation layer 120 is formed by first layer 122 and second layer 121 which are quilted together in some or all areas to integrally form a plurality of quilted compartments constituting the plurality of heaters 124. The plurality of heaters 124 formed from quilted compartments is most clearly shown in cross-sectional view of heat generation layer 120 in FIG. 2A. At least one of first layer 122 and second layer 121 is liquid permeable, and in some embodiments both layers may be liquid permeable, for example made from woven or non-woven fabric, paper or mesh. Some or all of heaters 124 include contain a first exothermic reactant 126, which may be any exothermically reactive material or combination of exothermic and non-exothermic materials as disclosed above.

Figure 2B:
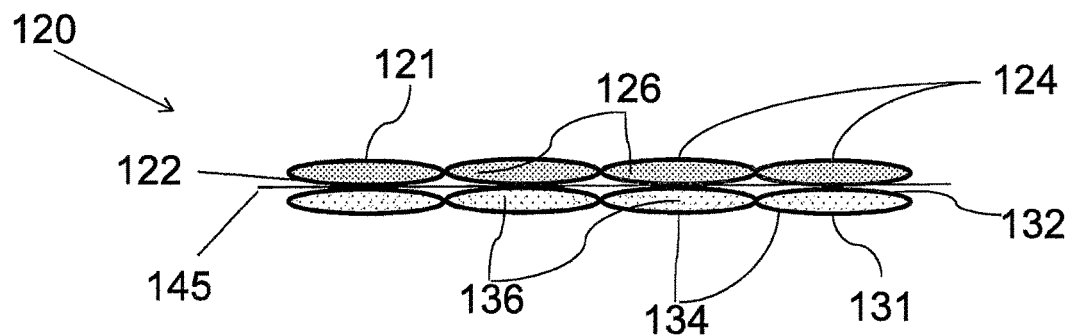

Another embodiment of heat generation layer 120 is shown in FIG. 2B. In FIG. 2B, heat generation layer 120 is formed by a first plurality of heaters 124 which in this embodiment, some or all of heaters 124 contain a first exothermic reactant 126. Heat generation layer 120 also comprises a second plurality of heaters 134 which in this embodiment, some or all of heaters 134 contain a second exothermic reactant 136. First plurality of heaters 124 is formed by quilted compartments, wherein each heater 124 contains a first layer 121 and a second layer 122. In some embodiments, a liquid permeable layer 145 is disposed between first plurality of heaters 124 and second plurality of heaters 134. In other embodiments, first 124 and second 134 plurality of heaters are bonded together by sonic welding, glue, or the like. Second plurality of heaters 134 may be formed by quilted compartments, wherein each heater 134 contains a first layer 131 and a second layer 132. Each of first 126 and second reactant 136 may be any exothermically reactive material or combination of exothermic and non-exothermic materials as disclosed above.

In the above-described multiple heating layer embodiment where instant heating and a long duration of heating are desired, at least one of the first exothermic reactants 126 or second exothermic reactants 136 is configured to heat much quicker and achieve approximately twice the temperature of the other. In certain embodiments, this is achieved through different compositions of first 126 and second 136 exothermic reactants. However, in other embodiments, this functionality is achieved by regulating the weight ratio of first 126 and second 136 exothermic reactants inside heat generation layer 120 (e.g., twelve parts second exothermic reactant 136 for every one part first exothermic reactant 126). Accordingly, as activator liquid permeates the first plurality of heaters 124, an initial exothermic reaction caused by first exothermic reactant 126 is caused that instantly heats up the blanket to the desired operational temperature. To sustain this heated temperature, activator liquid permeates the second plurality of heaters 134 with second exothermic reactant 136 with which is configured to produce heat for a longer duration of time.

In other embodiments, the composition and/or weight ratio of second reactant 136 and first reactant 126 may be switched such that it is instead the second plurality of heaters 134 that heats more quickly and/or is configured to heat to higher temperature whereas the first plurality of heaters 124 is configured to sustain the heated temperature for longer duration of time. In other words, the first 126 and second 136 exothermic reactants have different heating profiles, one having higher heated temperature yet heating for a shorter period of time, and the other configured to achieve lower heated temperature but for a longer period of time.

Figure 4:
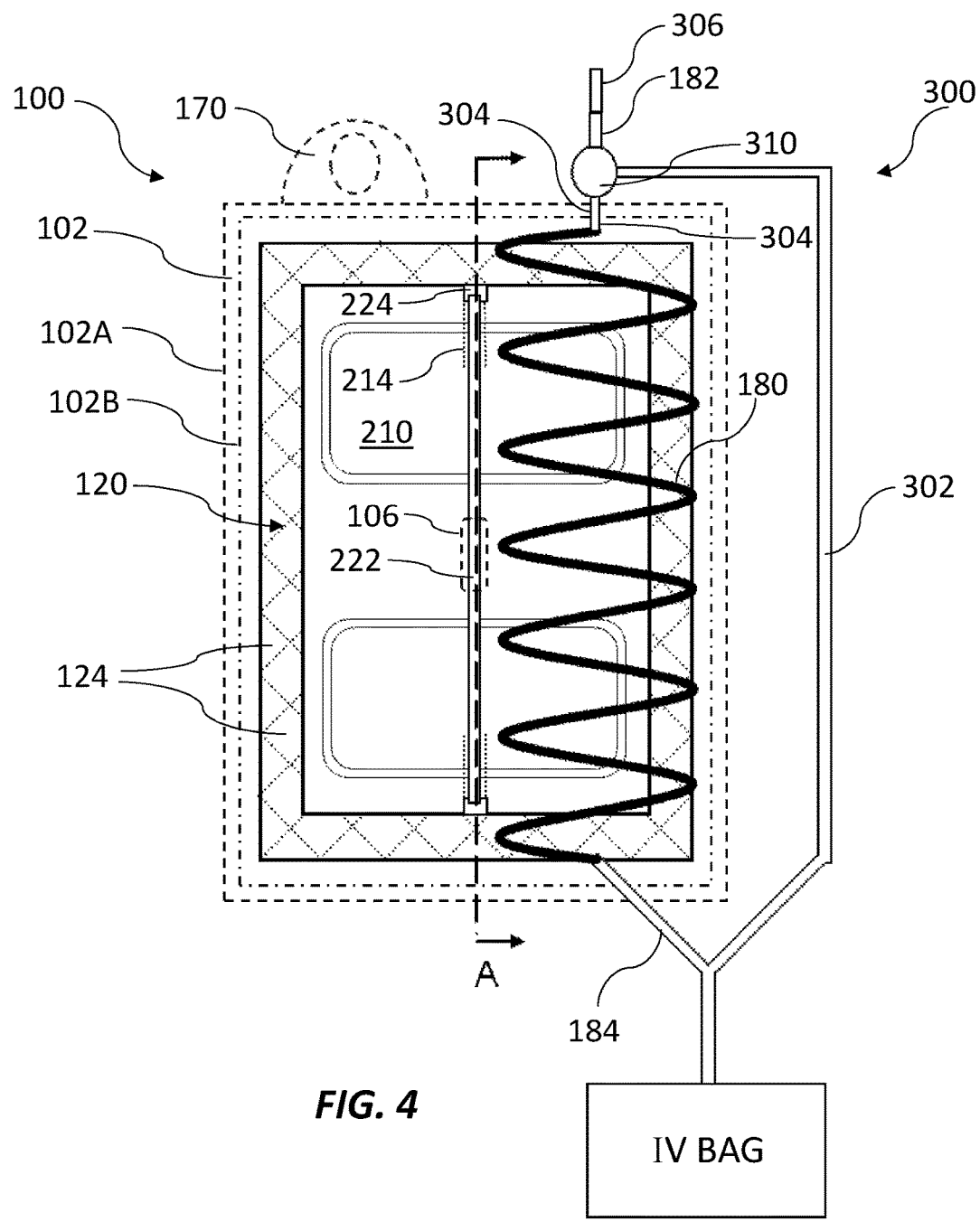
FIG. 4 shows the embodiment of FIG. 1 with an optional mixer valve for varying the temperature of fluids intravenously delivered to a user.

As shown in FIG. 4, another method of controlling the temperature of fluid flowing out of conduit 180 and into a blood vessel of a user is by providing temperature control system 300. Temperature control system 300 includes cooling inlet conduit 302, heating inlet conduit 304, outlet conduit 306 connected to outlet port 182 and mixer valve 310. Cooling inlet conduit 302 is in fluid communication with an source of fluid which may be unheated or below body temperature, which may be the same source of fluid that is connected to inlet port 184 of device 100, such as an IV bag. Heating inlet conduit 304 may be in fluid communication with outlet port 182 of device 100 though not necessarily in direct communication (i.e. in communication through mixer valve 310). Cooling inlet conduit 302 and heating inlet conduit 304 both connect to and are in fluid communication with mixer valve 310.

Outlet conduit 306 exits mixer valve 310. Mixer valve 310 selectively provides for outlet conduit 306 to be in fluid communication with only cooling inlet conduit 302, with only heated inlet conduit 304, or with both inlet conduits 302 and 304 simultaneously, sequentially, and/or in different amounts. This provides a user with the ability to regulate the temperature and amount of fluid to be delivered via outlet conduit 306.

Mixer valve 310 may be automatic and designed to always provide a mixture exiting outlet conduit 310 at a predetermined temperature or temperature range selected by a user, such as normal human body temperature. To accomplish this, mixer valve 310 may include a bimetallic strip inside mixer valve that controls the fluid mixture to outlet conduit 306. Accordingly, as the temperature of outlet conduit 306 changes, the bimetallic strip changes shape as well. This change in shape causes mixer valve 310 to modify the volume of fluid received from heating inlet conduit 304 and/or cooling inlet conduit 302 that intermix and exit outlet through conduit 306.

Alternatively, mixer valve 310 may be manually operated so that a user can manually adjust the amount of the mixture that flow from heating inlet conduit 304 and cooling inlet conduit 302 prior to exiting outlet conduit 306. A temperature display may be incorporated into temperature control system 300 so that the user can easily determine the temperature of outlet conduit 306 and adjust the mixture accordingly using mixer valve 310. The temperature display is operatively connected to outlet conduit 310 to determine its temperature. Temperature display may be an LCD or simple photochromatic strip that changes color with varying temperature. In certain embodiments, temperature control system 300 may be equipped with a user interface that can be operatively connected to the temperature display. A user interface provides the user with the ability to accurately monitor the temperature in the cooling inlet conduit 302, heating inlet conduit 304, and outlet conduit 306. Such user interfaces and means for monitoring fluid temperature are well known in the medical arts. Depend on needs of the patient, the user interface will provide the user with the ability to regulate the volumetric flow rate between the mixer valve 310, cooling inlet conduit 302, and heating inlet conduit 304 in order to precisely govern the temperature of the fluids being delivered to a patient.

The materials used in any of the disclosed embodiments may be any suitable materials in any combination. However, examples of some suitable materials for construction of intracorporeal fluid delivery device are as follows: the outer shell 102 may comprise one or more outer fabric layers 102A formed from a spun bonded nonwoven polypropylene or polyethylene, or a combination of both. However, in other embodiments, the outer layer 102A may be constructed from non-fabric material. The impermeable inner layer(s) 102B of the outer shell 102 may be coextruded polyethylene. The impermeable layer(s) 102B may be separate and distinct sheets or films, or may be formed by coated, laminating or extruding polyethylene directly onto the inner face of the fabric layer 102A of the outer shell 102.

The heat generation layer 120 may include any combination of woven and/or nonwoven fibers or sheets, including synthetic and/or natural materials. The liquid permeable heaters 124 may be formed by forming a quilted or celled liquid permeable structure from such materials, and impregnating the quilt, cells or chambers with exothermic reactants 126 and/or absorptive and/or super-absorptive gel-forming particles. For example, the cells may be impregnated with a powder mixture of exothermic reactants 126 and absorptive particles by radio frequency welding, sonic welding, laser welding, sewing, and/or adhesives. Further, the heat generation layer may comprise one or more layers of liquid permeable material and one or more layers of liquid impermeable material. For example, a liquid permeable nonwoven sheet impregnated with exothermic reactants may be coated or laminated on one side with a liquid impermeable film such as polyethylene. If so, the impermeable side of the heat generation layer 120 faces inward (toward the user's appendage), and the permeable side faces outward (although the opposite configuration may also be employed). There may be one, two or any other number of heat generation layers 120 in any number of combinations inside the internal enclosure 105 formed by the outer shell 102.

The exothermic reactant 126 and/or 136 in the heat generation layer 120 may include any known substance or mixture that undergoes an exothermic reaction when combined with a liquid activator. For example, a magnesium iron alloy reactive with an electrolyte solution may be used. In particular, Lava Gel® (Forever Young International Inc., Henderson, Nev.) is an ideal exothermic reactant mixture.

The heater activation system 200 may include bladders 210 made from a foil structure formed from multiple laminated layers such as oriented polypropylene, aluminum foil and polyethylene (in order from the outside of the device 100 to the inside). The foil structure may include pre-formed failure regions 214 such as etches including laser etches or perforations designed to easily sheer or burst open when the starter element 220 is pulled by the user. The starter element 220 may be a strip of any suitable material including a polymeric, fabric or metal foil adhered or welded to the bladder 210 or adjacent to the bladder 210 such that when pulled upon by a user, sheer lines, tears or cracks propagate to open or unseal the bladder 210. The activator liquid 202 inside the bladder(s) 210 may be any liquid that initiates an exothermic reaction when combined with the exothermic reactants in the heat generation layer, including water or an electrolyte solution such as salt water.

Figure 5:
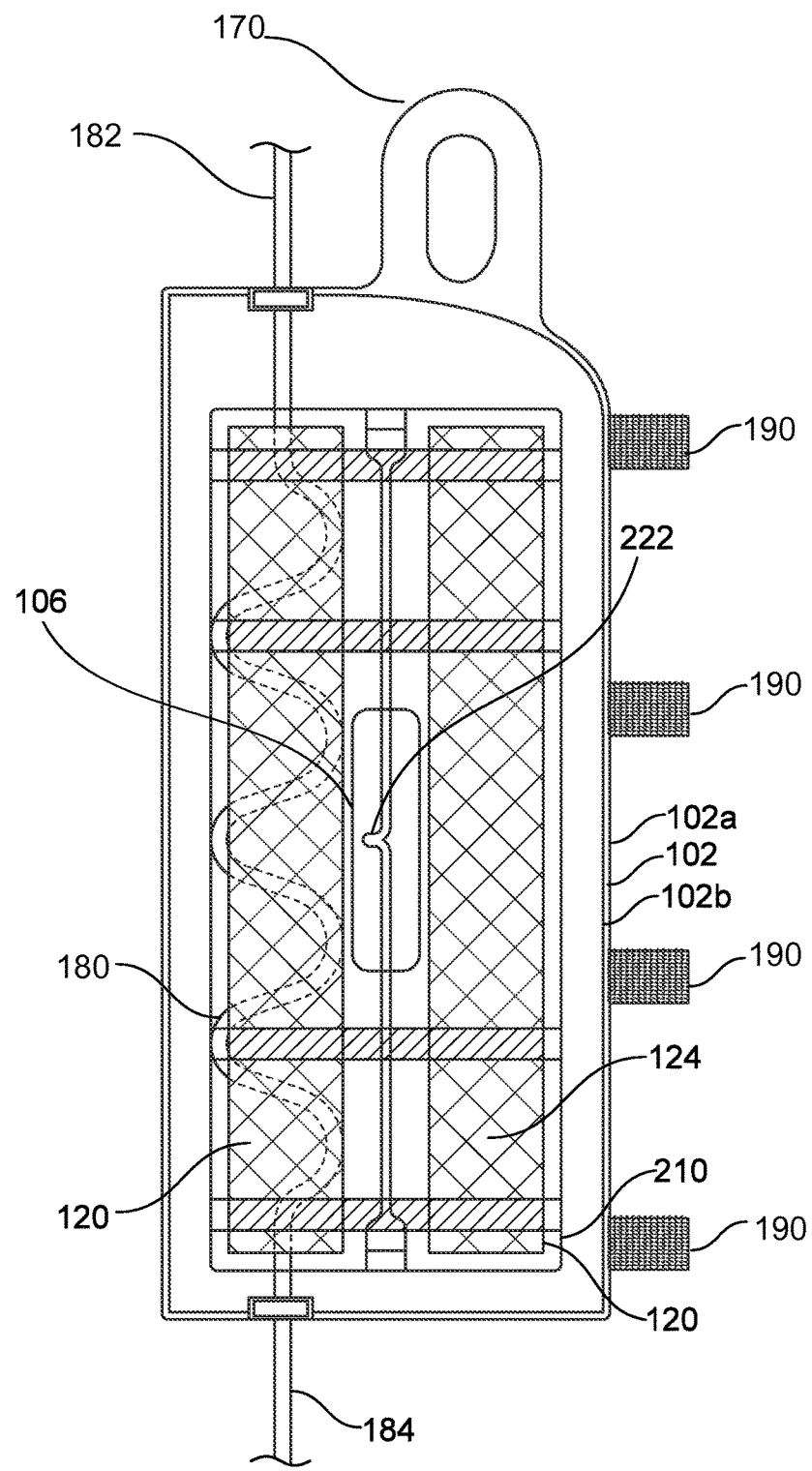
FIG. 5 shows an alternative view of the device depicted in FIG. 1.
Figure 6A:
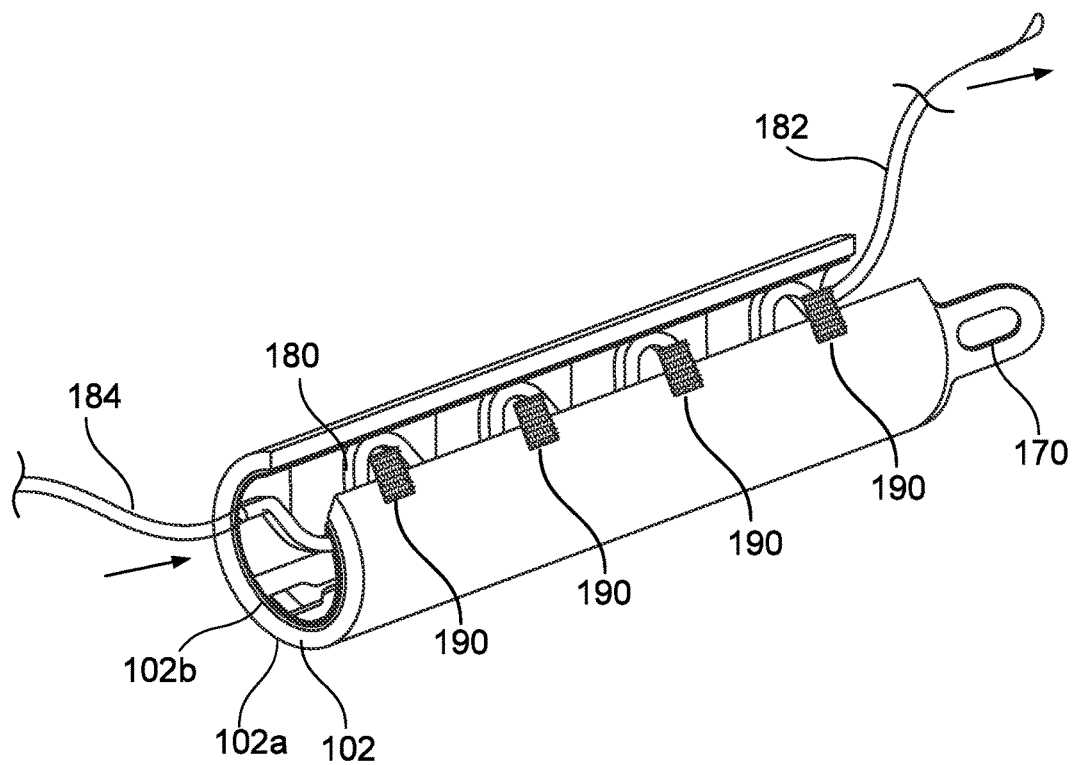
FIGS. 6a and 6b show different views of the device depicted in FIG. 3.
Figure 6B:
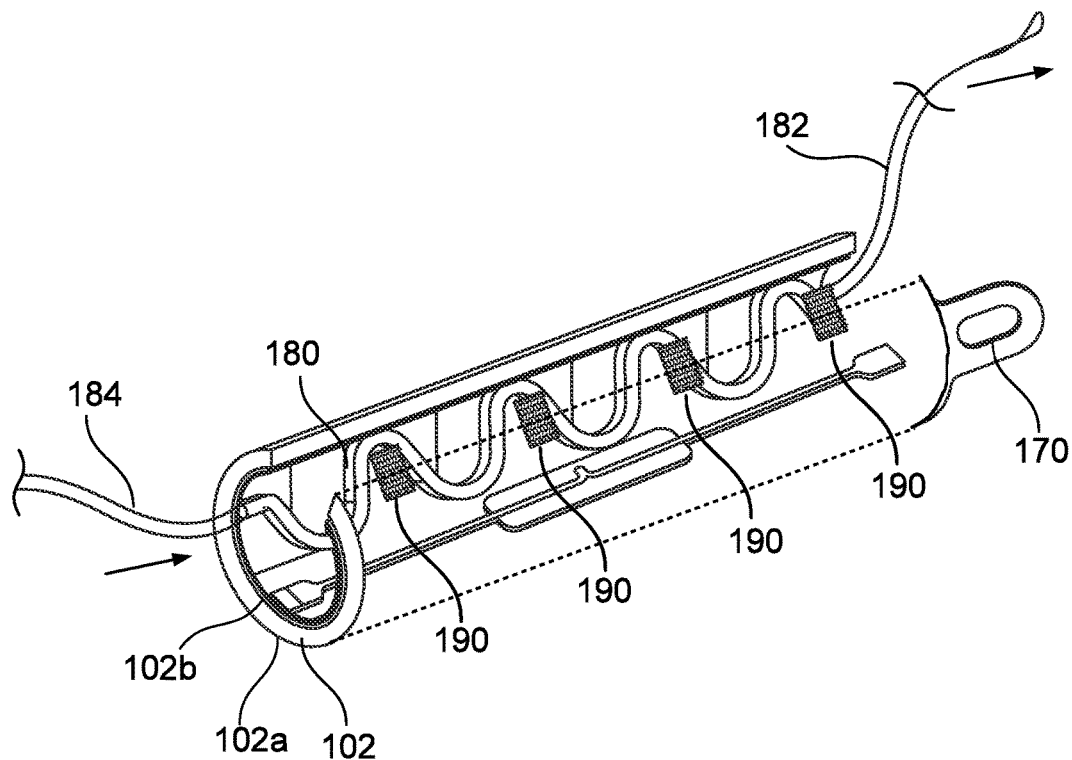

FIGS. 5, 6A and 6B depict alternative embodiments and views of the device 100 described herein.

The foregoing description only includes a few exemplary embodiments of the claimed subject matter. As it is impossible to describe every conceivable combination of components, features, steps and uses of the disclosed embodiments, the examples given above are not intended to define or limit the scope of the claimed subject matter, and those of ordinary skill in the art will realize that many other combinations not specifically set forth above are also possible. Finally, to the extent that the terms "having/has," "including/includes" or "comprising/comprises" are used above, these terms are intended to be open-ended and non-limiting unless the context clearly shows otherwise.

What is claimed is:

1. An intracorporeal fluid delivery device for heating a fluid to be administered to a patient, the device comprising:
    an outer shell, wherein the outer shell comprises an inner impermeable layer with an activation aperture, and an outer permeable layer, wherein the inner layer and the outer layer form an internal enclosure within the outer shell;
    a heat generation layer disposed inside the internal enclosure, wherein the heat generation layer comprises at least one first liquid permeable heater comprising a first exothermic reactant;
    an intracorporeal fluid conduit disposed within the outer shell or internal to the inner impermeable layer, wherein the intracorporeal fluid conduit has a path through the device, and wherein the intracorporeal fluid conduit further comprises an inlet port adjacent to a proximal end of the device and an outlet port adjacent to a distal end of the device; and
    a heater activation system disposed within the outer shell, comprising:
    at least one sealed bladder disposed inside the internal enclosure adjacent to the heat generation layer; and
    an activator liquid disposed in the at least one sealed bladder;
    wherein the activator liquid, when released from the at least one sealed bladder, contacts the heat generation layer and permeates the at least one first liquid permeable heater to combine with the first exothermic reactant causing a first exothermic reaction that heats fluid in the intracorporeal fluid conduit.

2. The device according to claim 1, further comprising a fastener configured to removably attach the device around an appendage of a patient.

3. The device according to claim 1, further comprising an activation strip operatively connected to the at least one sealed bladder, wherein the activation strip comprises a handle segment extending from the outer shell through the activation aperture into the at least one sealed bladder, wherein pulling the handle segment unseals the at least one sealed bladder and releases the activator liquid.

4. The device according to claim 1, wherein the distal end of the device comprises a thumb-receiving aperture for holding the device in place when disposed on an appendage of a patient.

5. The device according to claim 1, further comprising an outlet tube mechanically connected to the outlet port of the intracorporeal fluid conduit adapted for fluid communication with a vein of a patient, wherein the fluid is an intravenous fluid.

6. The device according to claim 1, further comprising an inlet tube mechanically connected to the inlet port of the intracorporeal fluid conduit adapted for fluid communication with a vein of a patient, wherein the fluid is an intravenous fluid.

7. The device according to claim 1, wherein the outer permeable layer of the outer shell comprises a fabric layer external to the inner impermeable layer, and wherein the intracorporeal fluid conduit is disposed between the inner impermeable layer and the outer fabric layer.

8. The device according to claim 1, wherein the intracorporeal fluid conduit is attached to the outer shell inside the internal enclosure.

9. The device according to claim 1, wherein the intracorporeal fluid conduit is routed nonlinearly between the inlet port and the outlet port.

10. The device according to claim 1, further comprising a temperature control system, wherein the temperature control system comprises:
    a cooling inlet conduit in fluid communication with a source of fluid wherein the fluid carried by the cooling inlet conduit is unheated by the heater activation system;
    a heating inlet conduit in fluid communication with the outlet port of the intracorporeal fluid conduit, wherein the cooling inlet conduit and the heating inlet conduit are in fluid communication with a mixer valve configured to regulate fluid flow in the temperature control system; and
    an outlet conduit in fluid communication with the mixer valve;
    wherein the mixer valve is configured to selectively provide for the outlet conduit to be in fluid communication with only the cooling inlet conduit, only the heating inlet conduit, or both the heating and cooling inlet conduits.

11. The device according to claim 10, wherein the mixer valve is configured to manually selectively provide for the outlet conduit to be in fluid communication with only the cooling inlet conduit, only the heating inlet conduit, or both the heating and cooling inlet conduits.

12. The device according to claim 10, further comprising a bimetallic strip disposed inside the mixer valve configured to automatically selectively regulate a volume of fluid flowing through the outlet conduit and automatically selectively provide for the outlet conduit to be in fluid communication with only the cooling inlet conduit, only the heating inlet conduit, or both the heating and cooling inlet conduits.

13. The device according to claim 1, wherein the heat generation layer further comprises at least one second liquid permeable heater comprising a second exothermic reactant;
    wherein the first exothermic reaction that heats fluids in the intracorporeal fluid conduit heats fluids in the intracorporeal fluid conduit to a first predetermined temperature for a first predetermined length of time;
    wherein the activator liquid contacts the heat generation layer and permeates the at least one second liquid permeable heater to combine with the second exothermic reactant causing a second exothermic reaction that heats fluids in the intracorporeal fluid conduit to a second predetermined temperature for a second predetermined length of time; and
    wherein the first predetermined temperature is greater than the second predetermined temperature and the first predetermined length of time is less than the second predetermined length of time.

14. The device according to claim 13, further comprising a liquid permeable layer disposed between the at least one first liquid permeable heater and the at least one second liquid permeable heater.

15. The device according to claim 1, further comprising at least one other heat generation layer, each heat generation layer exhibiting a different heating profile.

16. A temperature changing intracorporeal fluid delivery system comprising: the device according to claim 1; and
- a source of fluid configured for delivery to a patient, wherein the source of fluid is in fluid communication with the device.

17. The system according to claim 16, wherein the source of fluid is an intravenous fluid bag.

18. The device of claim 1, wherein the first exothermic reactant further comprises super-absorptive gel-forming particles and when the activator liquid combines with the first exothermic reactant, the first exothermic reaction forms a gel that heats fluid in the intracorporeal fluid conduit.

\* \* \* \* \*